United States Patent [19]

Verhoeven et al.

[11] Patent Number: 5,420,353
[45] Date of Patent: May 30, 1995

[54] REGIOSPECIFIC PROCESS TO MAKE CIS-1-AMINO-2-ALKANOL FROM EPOXIDE

[75] Inventors: Thomas R. Verhoeven, Cranford; F. Edward Roberts, Princeton; Christ H. Senanayake, North Brunswick; Kenneth M. Ryan, Skillman, all of N.J.

[73] Assignee: Merck & Co., Inc., Rahway, N.J.

[21] Appl. No.: 212,603

[22] Filed: Mar. 11, 1994

[51] Int. Cl.$^6$ ............................................ C07C 209/16
[52] U.S. Cl. ..................... 564/399; 548/217; 564/413; 564/415
[58] Field of Search ............... 564/399, 413, 428, 415; 548/217; 549/513, 546

[56] References Cited

U.S. PATENT DOCUMENTS

| | | | |
|---|---|---|---|
| 4,267,373 | 5/1981 | Hauck et al. | 564/428 |
| 4,518,528 | 5/1985 | Rasnick | 260/112.5 R |
| 4,888,445 | 12/1989 | Junino et al. | 564/441 |
| 5,244,915 | 9/1993 | Horwell et al. | 514/419 |

FOREIGN PATENT DOCUMENTS

| | | |
|---|---|---|
| 0541168 | 5/1993 | European Pat. Off. |
| 9005147 | 6/1982 | Japan |

OTHER PUBLICATIONS

R. Bishop, Comprehensive Organic Synthesis, ed. B. M. Trost and I. Fleming, vol. 6, pp. 271, 272, 276, 277, 297–298, (1991).
R. Oda, et al., Bull. Chem. Soc. Jap., vol. 35, p. 1219, (1962).
Bourgery, G. et al., Tetrahedron, vol. 28, pp. 1377–1390 (1972).
R. J. Ryan, Tetrahydron, vol. 29, pp. 3649–3654 (1973).
M. Imuta, et al., J. Organic Chem., vol. 43, p. 4540, (1978).
L. L. Sribnaya, et al., Zh. Org. Khim., vol. 10, p. 878, (1974).
Staub, H. A., Angevandte Chemie, vol. 74, p. 407, (1962).

*Primary Examiner*—Allen J. Robinson
*Assistant Examiner*—Brian M. Burn
*Attorney, Agent, or Firm*—Roy D. Meredith; Jack L. Tribble

[57] ABSTRACT

A regioselective process is disclosed for synthesis of 1R-amino-2S-indanol or 1S-amino-2R-indanol, wherein the stereochemical integrity of the carbon-oxygen bond at C-2 in the indene oxide starting material is retained.

5 Claims, No Drawings

REGIOSPECIFIC PROCESS TO MAKE CIS-1-AMINO-2-ALKANOL FROM EPOXIDE

BACKGROUND OF THE INVENTION

The present application is related to Merck 18996, U.S. Ser. No. 08/059,038, filed May 7, 1993, and Merck case 19115, U.S. Ser. No. 08/212,604, filed Mar. 11, 1994.

The present invention is concerned with a novel intermediate and process for synthesizing compounds which inhibit the protease encoded by human immunodeficiency virus (HIV), and in particular certain oligopeptide analogs, such as compound J in the Examples below. These compounds are of value in the prevention of infection by HIV, the treatment of infection by HIV and the treatment of the resulting acquired immune deficiency syndrome (AIDS). These compounds are also useful for inhibiting renin and other proteases.

The invention described herein concerns a process to effect the regiospecific generation of a cis-1-amino-2-alkanol, particularly cis-1-amino-2-indanol (Compound B), from an epoxide precursor. More specifically, the stereochemical integrity of the carbon-oxygen bond at C-2 in the indene oxide., starting material is retained, so that there is substantially complete ,conversion to the appropriate product 1-amino-2-indanol. For example, (1S,2R)-indene oxide produces substantially 1S-amino-2R-indanol, and (1R,2S)-indene oxide produces substantially 1R-amino-2S-indanol. Mixtures of epoxide enantiomers produce substantially the same mixture of 1-amino-2-indanol enantiomers. The process described is superior to prior art in that the process is shorter, more productive, and has higher yields with less environmental impact.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313,277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, compound J therein.

Previously., the synthesis of Compound J and related compounds was accomplished via a 12-step procedure. This procedure is described in EPO 541,168. The extreme length of this route (12 steps), renders this process time consuming and labor intensive, and it requires the use of many expensive reagents and an expensive starting material. A route requiring fewer reaction steps and reagents would provide desirable economical and time-saving benefits.

Specifically, the invention provides a process for the synthesis of 1S-amino-2R-indanol (Compound B) from (1S,2R)-indene

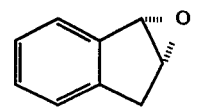

A

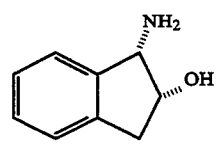

B oxide (Compound A). The epoxide A is treated with a strong acid and a nitrile, then hydrolyzed with water to give the target Compound B. The process of the present invention is a one step procedure, and avoids isolation of any intermediate.

The preparation of 1-amino-2-indanol was previously accomplished via a multistep sequence. This sequence involved the treatment of an indene oxide with aqueous ammonia to produce a trans-1-amino-2-indanol (Cpd C).

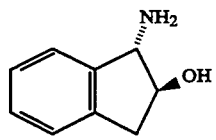

Cpd C

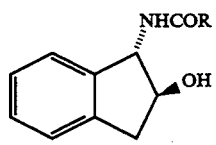

Cpd D

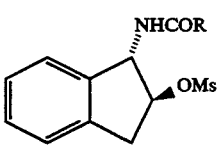

Cpd E

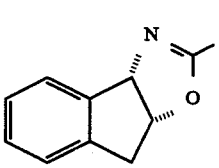

Cpd F

The intermediate C is then treated with an acyl halide, thereby converting the amine to an amide intermediate (Cpd D). The hydroxyl group of the hydroxy amine D is activated by conversion to a mesylate (Cpd E), which is then induced to cyclize and form the oxazoline F. The oxazoline F produced by this prior art method is purified, then subjected to conditions similar to that described above effecting its conversion to the target cis-1-amino-2-indanol.

In previous attempts, epoxides are reported to give only poor yields of regioisomeric oxazolines when subject to the conditions of strong acid/nitrile solvents. See R. Bishop, "*Comprehensive Organic Synthesis,*" ed. B. M. Trost et al., Pergamon Press. New York, 1991, vol. 6 p. 276; R. Oda, et al., Bull. Chem. Soc. Jpn., 35, 1219 (1962).

Contrary to the present invention, steroidal epoxides when treated with acid and a nitrile are reported to produce transdiaxial alpha amido alcohols and not oxazolines [G. Bourgery, et al., Tetrahedron, 28, 1377 (1972); R. J. Ryan etal., Tetrahedron, 29, 3649 (1973)].

Also contrary to the present invention, methyl-trans-2-epoxystearate is reported to produce an erythro-beta amino-alcohol and not an oxazoline [E. N. Zvankova and R. P. Evstigneeva, Zh. Org. Khim., 10, 878, (1974)].

Thus related art teaches that treatment of an epoxide under the conditions described by this invention would not only be expected to produce low yields but also the wrong product.

The process of the present invention provides a route with fewer chemical steps to accomplish the same overall synthesis of 1S-amino-2R-indanol. Furthermore, the isolation of intermediates is not necessary in the present invention. Also, the present process utilitizes smaller quantities of organic solvents and proceeds in greater overall yield than prior methods, a result providing lower environmental impact than prior methods.

BRIEF DESCRIPTION OF THE INVENTION

The present invention provides new methods to effect the regiospecific generation of a (1S, 1R)-amino-(2R, 2S)-alkanol, particularly 1S-amino-2R-indanol. The process of the present invention substantially retains the stereochemical integrity of the carbon-oxygen bond of the (1S, 1R)-amino-(2R,2S)-alkanol starting material. The product compounds are intermediates for compounds useful in the synthesis of inhibitors of HIV protease, renin and other proteases.

DETAILED DESCRIPTION OF THE INVENTION

The present invention provides new methods for making the enantiomeric intermediates 1-amino-2-alkanol, particularly 1S-amino-2R-indanol or 1R-amino-2S-indanol. These intermediates are useful for the preparation of HIV protease inhibitors.

In this invention, a regioselective process is disclosed for synthesizing any enantiomer of cis-1-amino-2-indanol or mixture of said enantiomers, said process substantially retaining the stereochemical integrity of the carbon-oxygen bond at C-2 in the indene oxide starting material, wherein the process comprises the steps of
  (a) providing one equivalent of indene oxide dissolved in a solvent and, optionally, a co-solvent, said solvent selected from an alkyl nitrile or aryl nitrile;
  (b) mixing thereto about two equivalents of an acid, said acid selected from a strong protic acid or a Lewis acid or an organic acid, and maintaining thereafter the temperature of the resulting mixture between about −70° C. and about +30° C. for a time period of between about 0.25 hour and about 6.0 hours;
  (c) adding excess water to effect hydrolysis, and stirring for a time period of between about 0.5 hour and about 8.0 hours, at a temperature of between about 25° C. and about 100° C., to give the corresponding enantiomer of cis-1-amino-2-indanol, or mixture of said enantiomers.

In this particular application, starting material indene oxide (Cpd A shows the 1S,2R enantiomer) is readily synthesized by a variety of methods. The starting material indene oxide, in any mixture of enantiomers including racemic and optically pure forms, is treated with a strong protic acid, such as sulfuric acid or $H_2SO_4$-$SO_3$, or Lewis acid such as boron trifluoricle, or an organic acid such as p-toluenesulfonic acid, methanesulfonic acid, trifluoroacetic acid or trifluoromethanesulfonic acid. The reaction may be carried out in a mixture of a solvent and, optionally, a co-solvent, the solvent consisting of alkyl nitrile or aryl nitrile, e.g., acetonitrile, propionitrile, or benzonitrile. The cosolvent includes, but is not limited to, hydrocarbons, such as hexanes, heptanes or toluene, or halocarbons, such as dichloromethane or chlorobenzene. Other conditions include a temperature of between about −70° C. to about +30° C., and an incubation period ranging from about 0.25 to about 6.0 hours. The presence of water in these steps, (a) and (b), is not necessary and in some cases gives undesired results. The product of step (b) appears to be the oxazoline of general structure F (here the 1S,2R form) in a yield with the range of approximately 50–85%.

Although possible, it is unnecessary to isolate the intermediate oxazoline F. Preferably, unisolated oxazoline F is directly treated with water for a period of about 0.5 to about 8 hours at a temperature in the range of about 25°–100° C. This effects hydrolysis of the oxazoline and produces the 1S-amino-2R-indanol (Cpd B). Isolation of this product as either its crystalline free base (i.e. amino-indanol) or as an amine salt derivative (e.g. a tartaric acid salt) is accomplished directly from the reaction medium by pH adjustment to provide this amino indanol intermediate. The overall yield, that is, the yield of steps (a) through (c) above, ranges from about 50% to about 80%.

In one embodiment of regioselective process of the present invention, (1S,2R)-indene oxide is substantially converted to 1S-amino-2R-indanol, by the steps of:
  (a) providing one equivalent of (1S,2R)-indene oxide dissolved in a solvent and, optionally, a co-solvent, said solvent selected from an alkyl nitrile or aryl nitrile;
  (b) mixing thereto about two equivalents of an acid, said acid selected from a strong protic acid or a Lewis acid or an organic acid, and maintaining thereafter the temperature of the resulting mixture between about −70° C. and about +30° C. for a time period of between about 0.25 hour and about 6.0 hours;
  (c) adding excess water to effect hydrolysis, and stirring for a time period of between about 0.5 hour and about 8.0 hours, at a temperature of between about 25° C. and about 100° C., to give 1S-amino-2R-indanol substantially free of any other enantiomer.

In another embodiment of regioselectiveprocess of the present invention, (1R,2S)-indene oxide is substantially converted to 1R-amino-2S-indanol, by the steps of:

(a) providing one equivalent of (1R,2S)-indene oxide dissolved in acetonitrile and, optionally, a co-solvent;

(b) mixing thereto about two equivalents of an acid selected from methanesulfonic acid or $H_2SO_4$-$SO_3$, and maintaining thereafter the temperature at about $-10°$-$25°$ C. for a time period of between about 30 minutes and about 2.5 hours;

(c) adding excess water to effect hydrolysis, and stirring for time period between about 2 and about 5 hours, at a temperature range between about 45° C. and about 100° C., to give 1R-amino-2S-indanol substantially free of any other enantiomer.

Another embodiment of the present invention is the regioselctive process, of synthesizing 1S-amino-2R-indanol, comprising the steps of (a) providing one equivalent of (1S,2R)-indene oxide dissolved in acetonitrile and, optionally, a co-solvent;

(b) mixing thereto about two equivalents of an acid selected from methanesulfonic acid or $H_2SO_4$-$SO_3$, and maintaining thereafter the temperature at about $-10°$-$25°$ C. for a time period of between about 30 minutes and about 2.5 hours;

(c) adding excess water to effect hydrolysis, and stirring for time period between about 2 and about 5 hours, at a temperature range between about 45° C. and about 100° C., to give 1S-amino-2R-indanol substantially free of any other enantiomer.

Another embodiment of the present invention is the regioselective process of synthesizing 1R-amino-2S-indanol, comprising the steps of (a) providing one equivalent of (1R,2S)-indene oxide dissolved in acetonitrile and, optionally, a co-solvent;

(b) mixing thereto about two equivalents of an acid selected from methanesulfonic acid or $H_2SO_4$-$SO_3$, and maintaining thereafter the temperature at about $-10°$-$25°$ C. for a time period of between about 30 minutes and about 2.5 hours;

(c) adding excess water to effect hydrolysis, and stirring for time period between about 2 and about 5 hours, at a temperature range between about 45° C. and about 100° C., to give 1R-amino-2S-indanol substantially free of any other enantiomer.

The processes and intermediates of this invention am useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,164. The HW protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and[occur as racemates, racemic mixtures and as individual diastereomers, or enantiomers with all isomeric forms being included in the present invention.

When any variable (e.g., aryl) occurs more than one time in any constituent, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl); As used herein, "aryl" is intended to mean phenyl (Ph) or naphthyl.

Representative experimental procedures utilizing the novel process are detailed below. These procedures are exemplary only and are not limitations on the novel process of this invention.

EXAMPLE 1

Conversion of Indene Oxide to Cis-1-Amino-2-Indanol

| Materials | Mol. Wt. | Grams or ml | Millimoles |
|---|---|---|---|
| Indene oxide | 132 | 1 ml | 8.33 |
| Acetonitrile | 41 | 10 ml | 244 |
| Water | 18 | 2.15 ml | 119.4 |
| Conc. $H_2SO_4$ | 98 | 0.92 ml | 16.6 |
| 5N KOH | 57 | 3.0 ml | 15 |
| Dowex 50 × 4 (H+) | 1.9 meq/ml | 15 ml wet resin | 28.5 meq |
| Methanol | 17 | 50 ml | 50 |

To one ml of indene oxide (8.33 mmoles) dissolved in 10 ml acetonitrile was added 0.15 ml water (8.33 mmoles). The mixture was cooled to 0°-5° in an ice bath. Concentrated sulfuric acid was added dropwise while maintaining the batch temperature below 10°. When all the acid was added and the temperature was allowed to rise to 20°-25°. The clear solution was aged for 30 minutes.

To this mixture was added 2 ml of water and the solution heated for 30 minutes. When the methyl oxazoline was completely coverted to cis amino indanol the reaction mixture was cooled to room temperature.

A solution of 5N KOH (3 ml, 15 mmoles) was added. This is 90% of theory for the sulfuric acid. The solution remained acid to litmus. If the pH rises above, 2 re-acylation occurs and the yield of amino indanol is reduced. The white solid (K₂SO₄) was removed by filtration.

Dowex resin 15 ml (wet with acetonitrile) was added with stirring. The stirred resin was aged for 15 minutes and sampled for LC (dilx 50). When the LC peak for amino indanol disappeared, the resin was collected by filtration, washed with acetonitrile and then with methanol.

The wet resin was treated with a solution of 50 ml 1N NH₃ in methanol and the slurry stirred at room temperature for 30 minutes. The resin was again collected by filtration and the methanol/NH₃ saved. Another charge of 1N NH₃/MeOH (20 ml) was added and the resin reslurried. After removal of the resin the methanol/NH₃ solutions of the amino indanol were combined and concentrated to remove the NH₃. Analysis of the final MeOH solution shows 1.0 g (81% yield) cis-1-amino-2-indanol ready for the tartaric acid resolving agent.

EXAMPLE 2

Preparation of Racemic Indene Oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1M aqueous NaOH (39 mL). Water (700 mL) was added and the mixture extracted with methylene chloride (580 mL and 300 mL). The combined organic extracts containing indene oxide (117 g) were concentrated to a volume of 600 mL.

EXAMPLE 3

Preparation of (1S, 2R)-indene oxide

The substrate, (1S, 2R)-indene oxide is prepared according to the method described by D. J. O'Donnell, et al., J. Organic Chemistry, 43, 4540 (1978), herein incorporated by reference for these purposes.

EXAMPLE 4

Preparation of cis- 1-amino-2-indanol

Indene oxide (117 g) diluted to a total volume of 600 mL in methylene chloride was diluted with acetonitrile (600 mL) and cooled to −20° C. Methanesulfonic acid (114 mL) was then added. The mixture was warmed to 25° C. and aged for 2 h. Water (600 mL) was added and the mixture heated at 45° C. for 5 h. The organic phase was separated and the aqueous phase further heated at reflux for 4 h with concentration to approximately 200 g/L. The solution was adjusted to pH 12.5 with 50% aqueous sodium hydroxide, and then cooled to 5° C. and filtered, dried in vacuo, to provide cis 1-amino-2-indanol.

EXAMPLE 5

Preparation of 1S-amino-2R-indanol (1,S, 2R)-indene oxide (85% ee,) (250 g, 0.185 mole) was dissolved in chlorobenzene (300 mL) and heptanes (1200 mL) and slowly added to a solution of methanesulfonic acid (250 mL, 0.375 mole) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2-3 h then cooled to room temperature. Chlorobenzene (1000 mL) was added, the mixture stirred, the organic phase separated. The remaining aqueous phase containing 1S-amino, 2R-indanol (85% ee, 165 g, 60%) was adjusted to pH 12 with 50% aqueous sodium hydroxide and the product collected by filtration and dried in vacuo at 40° C. to yield 1S-amino, 2R-indanol (85% ee, 160 g).

EXAMPLE 6

Preparation of 1S-amino-2R-indanol (1S, 2R)-indene oxide (85% ee,) (250 g, 0.185 mole) was dissolved in chlorobenzene (300 mL) and heptanes (1200 mL) and slowly added to a solution of fuming sulfuric acid (21% SO₃, 184 mL) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2-3 h, then cooled to room temperature. Chlorobenzene (1000 mL) was added, the mixture stirred, the organic phase separated. The remaining aqueous phase containing 1S-amino, 2R-indanol (85% ee, 205 g, 74%) was diluted with an equal volume of acetonitrile. The pH was adjusted to 12.5 with 50% aqueous sodium hydroxide and the organic phase separated. The remaining aqueous phase was extracted with additional acetonitrile. The combined acetonitrile extracts were concentrated in vacuo to provide 1S-amino, 2R-indanol (85% ee, 205 g).

Alternatively, the remaining aqueous phase containing 1S-amino-2R-indanol (85% ee, 205 g, 74%) was diluted with an equal volume of butanol and the pH was adjusted to 12.5 with 50% aqueous sodium hydroxide and the organic phase separated. The organic phase was washed with chlorobenzene. L-tartaric acid was added and water was removed by distillation to crystallize the tartaric acid salt of the amino-indanol.

EXAMPLE 7

Use of benzonitrile

Indene oxide (5 g) was dissolved in benzonitrile (50 mL) at 25° C. and sulfuric acid (98%, 2.25 mL) was added. The mixture was diluted with 5M aqueous sodium hydroxide solution (50 mL) and extracted with methylene chloride. The organic extracts were concentrated in vacuo to give 5.03 g of oxazoline.

EXAMPLE 8

Resolution of cis-1-Amino-2-indanol

Cis-1-Amino-2-indanol (100 g) was dissolved in methanol (1500 mL) and a solution of L-tartaric acid (110 g) in methanol (1500 mL) was added. The mixture was heated to 60° C. and cooled to 20° C., filtered and dried in vacuo to give 1S-amino, 2R-indanol L-tartaric acid salt as a methanol solvate (88 g).

EXAMPLE 9

Preparation of 1S-Amino-2R-indanol

1S-Amino, 2R-indanol L-tartaric acid salt methanol solvate (88 g) was dissolved in water (180 mL) and heated to 55°-60° C. The solution was clarified by filtration and the pH adjusted to 12.5 with 50% aqueous sodium hydroxide. The mixture was cooled to 0°–5° C. over 2 h, then aged at that temperature for 1 h, filtered, washed with cold water and dried in vacuo at 40° C. to yield 1S-amino, 2R-indanol (100% ee, 99% pure, 37 g).

EXAMPLE 10

Preparation of Amide 1

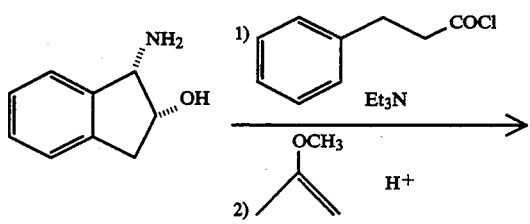

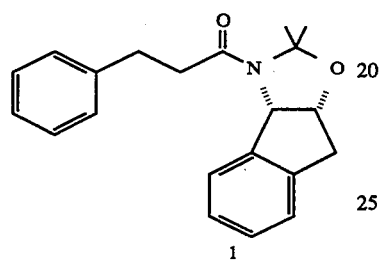

A solution of (−)-cis-1-aminoindan-2-ol (884 g, 5.93 mol) in 17.8 L of dry THF (KF =55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10mM ($KH_2PO_4/K_2HPO_4$), 1.0 mL/min., injection volume=20 mL, detection=200 nm, sample preparation=500 X dilution. Approximate retention times:

| retention time (min.) | identity |
|---|---|
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 1 (86.4%, 98 area % by HPLC), $^1H$ NMR (300.13 MHz, $CDCl_3$, major rotamer) δ7.36–7.14 (m, 9 H), 5.03 (d, J=4.4, 1 H), 4.66 (m, 1 H) 3.15 (m, 2 H), 3.06 (br s, 2 H), 2.97 (m, 2 H), 1.62 (s, 3 H), 1.37 (s, 3 H); $^{13}C$ NMR (75.5 MHz, $CDCl_3$, major rotamer) $δ_c$ 168.8, 140.9, 140.8, 140.6, 12,8.6, 128.5, 128.4, 127.1, 126.3, 125.8, 124.1, 96.5, 78.6, 65.9, 38.4, :36.2, 31.9, 26.5, 24.1: Anal. Calcd for $C_{21}H_{23}NO_2$: C, 78.47; H, 7.21; N, 4.36. Found: C, 78.65; H, 7.24; N, 4.40.

EXAMPLE 11

Preparation of Epoxide 3
Tosylate Method

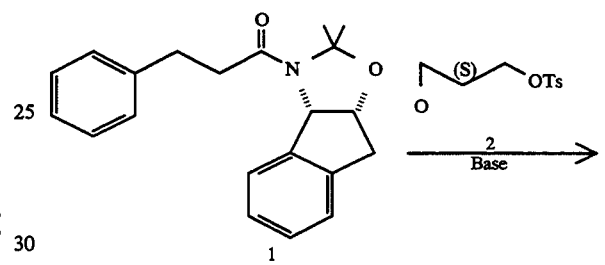

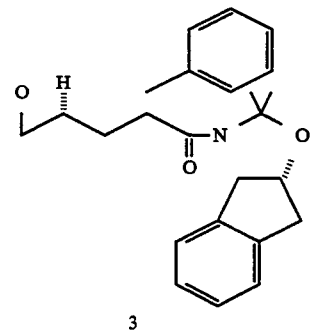

A solution of acetonide 1 (1000 g, 3.11 mol) and 2(S)-glycidyl tosylate 2 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide ($LiN[(CH_3)_3Si]_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm X 4.6 nm Zorbax Silica column, 20% ethyl acetate in hexane, 2.0 mL/min, injection volume=20 mL, detection =254 nm, sample preparation=100×dilution. Approximate retention times:

| retention time (min.) | identity |
|---|---|
| 5.5 | amide 1 |

| retention time (min.) | identity |
|---|---|
| 6.5 | glycidyl tosylate 2 |
| 13.5 | epoxide 3 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous NaHCO$_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 3 (61.2%, 98.7 area % of the major epoxide by HPLC): $^{13}$C NMR (300 MHz, CDCl$_3$) δ 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 17

Preparation of penultimate 6

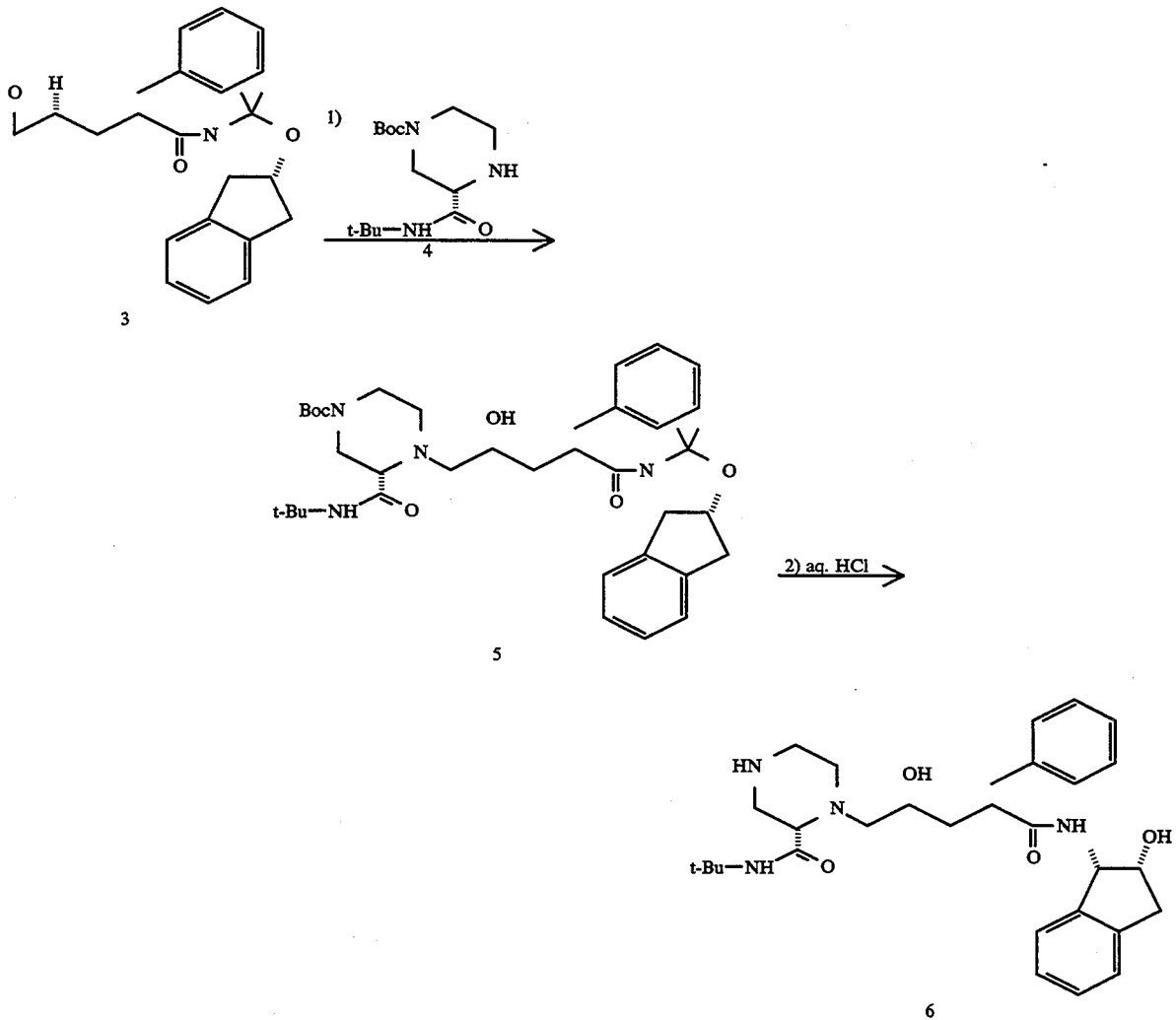

A slurry of the 2(S)-t-butylcarboxamide-4-N-Boc-piperazine 4 (1950 g, 6.83 mol, >99.5% ee) (ee=enantiomeric excess) and the epoxide 3 (2456 g, 97.5:2.5 mixture of 4S/R epoxides, 6.51 mol) in isopropanol (2.-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM (KH$_2$PO$_4$/K$_2$HPO$_4$), 1.0 mL/min., detection=220 nm, sample preparation=2 μL, reaction mixture diluted to 1 mL in acetonitrile. Approximate retention times:

| retention time (min) | identity |
| --- | --- |
| 4.8 | piperazine 4 |
| 8.9 | epoxide 3 |
| 15.2 | coupled product 5 |

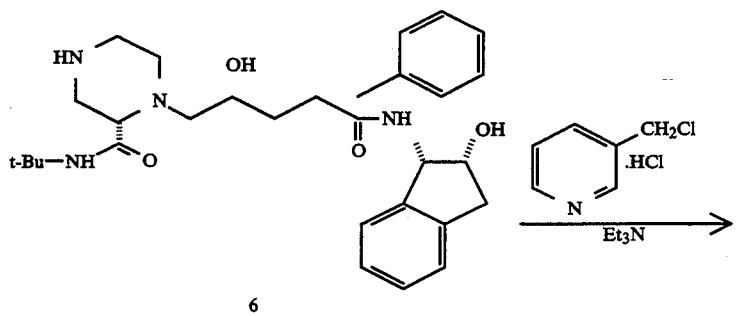

6

After 28 h, the remaining epoxide 3 and coupled product 5 (by HPLC analysis) were 1.5 area % and 91–93 area %, respectively. The mixture was cooled to 0° to 5° C. and 20.9 L of 6 N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
| --- | --- |
| 7.0 | cis-aminoindanol |
| 11.9 | penultimate 6 |
| 15.1 | coupled product 5 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 6 in ethyl acetate was 86.5%. The penultimate compound 6 in DMF was directly used in the next step without further purification. For isolated 6: $^{13}$C NMR (75.4 MHz, CDCl$_3$) δ175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 13

Preparation of monohydrate of Compound J

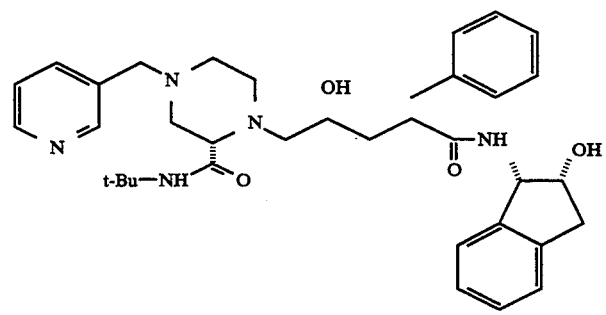

7

Compound J

The solution of 6 in DMF (10.5 L, KF=10 mg/mL) from the previous step was charged with 8 L of sieve dried DMF (KF. <30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

| Retention time (min) | Identity |
| --- | --- |
| 2.7 | DMF |
| 4.2 | 3-picolyl chloride |
| 4.8 | Compound J |
| 9.1 | penultimate 6 |

The mixture was aged at 68° C. until the residual penultimate compound 6 was <0.3 area % by HPLC analysis.

The mixture was stirred at 68° C. for 4 h, then cooled to 25° C. and partitioned with ethyl acetate (80 L) and a mixture of 24 L of saturated aqueous NaHCO$_3$ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

EXAMPLE 14

Pyrazine-2-tert-butyl carboxamide 9

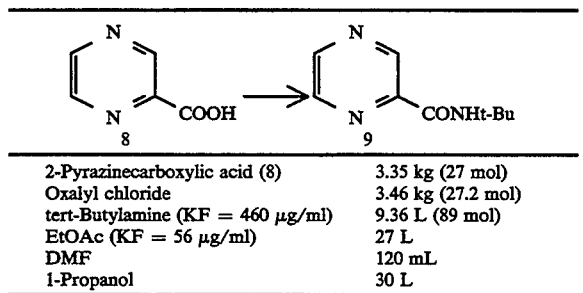

| | |
|---|---|
| 2-Pyrazinecarboxylic acid (8) | 3.35 kg (27 mol) |
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 8 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 8 remained.

The assay for completion of the acid chloride formation is important because incomplete reaction leads to formation of a bis-tertbutyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 8=10.7 min, amide 9=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 9 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol-/EtOAC solution of 3 was stable to reflux atatmospheric pressure for several days.

Evaporation of an aliquot gave a tan solid m.p 87°–88° C. $^{13}C$ NMR (75 MHz, CDCl$_3$, ppm) 161.8, 146.8,145.0, 143.8, 142.1, 51.0, 28.5.

EXAMPLE 15 rac-2-tert-Butyl-carboxamide-piperazine 10

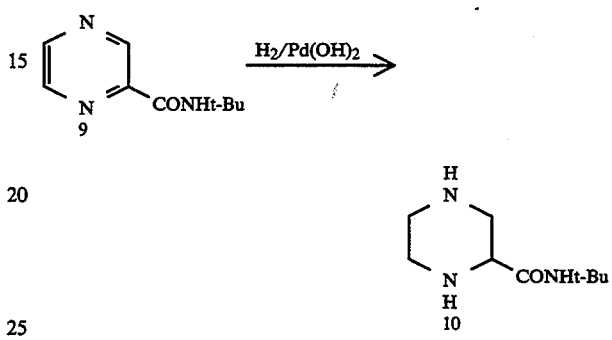

Materials

Pyrazine-2,-tert-butylcarboxamide 9 2.4 kg (13.4 mol) in 1-Propanol solution 12 L 20% Pd(OH)$_2$/C 16 wt. % water 144 g The pyrazine-2-tert-butylcarboxamide 9/1-propanol solution was placed into the 5 gal autoclave. The catalyst was added and the mixture was hydrogenated at 65° C. at 40 psi (3 atm) of $H_2$.

After 24 h. the reaction had taken up the theoretical amount of hydrogen and GC indicated <1% of 9. The mixture was cooled, purged with $N_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 9=7.0 min, 10=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 10 is 33g/L.

Evaporation of an aliquot gave 10 as a white solid m.p. 150°–151° C.; $^{13}C$ NMR (75 MHz, D$_2$O, ppm) 173.5, 59.8, 52.0, 48.7, 45.0, 44.8, 28.7.

EXAMPLE 16

(S)-2-ten-Butyl-carboxamide-piperazine bis (S)-Camphorsulfonic acid salt (S)-11

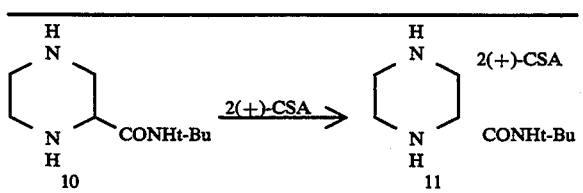

Materials rac-2-tert-Butyl-carboxamide-piperazine 10    4.10 kg (22.12 mol)

-continued

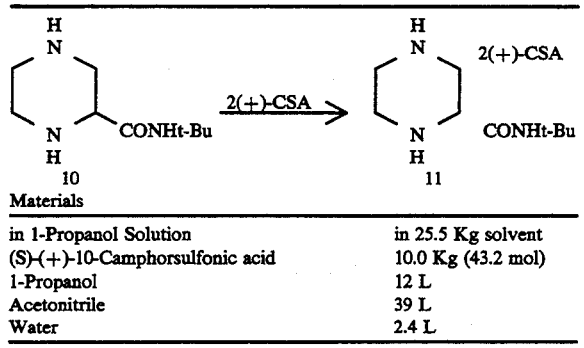

| Materials | |
|---|---|
| in 1-Propanol Solution | in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 10 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 10 was 341 g/L The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 10:2.5 min.

Acetonitrile (39 L) and water (2.4 L) were added to give a clear, slightly brown solution.

Determination of the water content by KF titration and $CH_3CN/1$-propanol ratio by $^1H$ NMR integration showed that the $CH_3CN/1$-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21 ° C. over 8 h.

The product precipitated at 62° C. The product was filtered without aging at 21 ° C., and the filter cake was washed with 5 L of the $CH_3CN/1$-propanol/$H_2O$ 26/8/1.6 solvent mixture. It was dried at 35° C. in the vacuum oven with $N_2$ bleed to give 5.6 Kg (39%) of 11 as a white crystalline solid m.p 288°-290° C. (with decomp.) $[\alpha]D^{25}=18.9°$ (c=0.37, $H_2O$). $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 11 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 17

(S)-2-tert-Butylcarboxamide-4-tert-butoxycarbonyl-piperazine 4 from salt 11

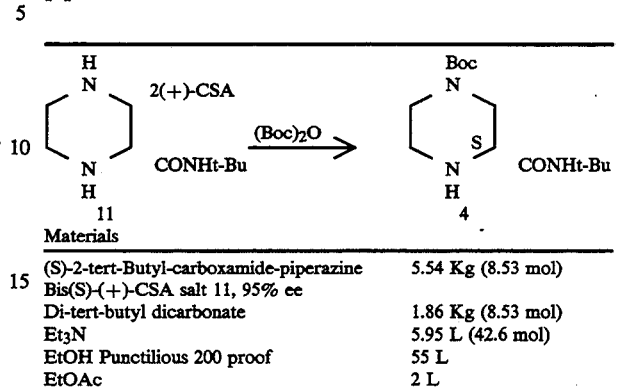

| Materials | |
|---|---|
| (S)-2-tert-Butyl-carboxamide-piperazine Bis(S)-(+)-CSA salt 11, 95% ee | 5.54 Kg (8.53 mol) |
| Di-tert-butyl dicarbonate | 1.86 Kg (8.53 mol) |
| $Et_3N$ | 5.95 L (42.6 mol) |
| EtOH Punctilious 200 proof | 55 L |
| EtOAc | 2 L |

To the (S)-CSA salt 11 in a 100 L 3-neck flask with an addition funnel under $N_2$ was added EtOH, followed by triethylamine at 25° C. The solid dissolved readily on the addition of the $Et_3N$. The $Boc_2O$ was dissolved ha EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC:25 cm Dupont Zorbax RXC8 column with 1 mL/min flow and detection at 228 nm, isocratic (50/50) $CH_3CN/0.1M$ $KH_2PO_4$ adjusted to pH=6.8 with NaOH. Retention time: of 4=7.2 min. The chiral assay was carded out using the same system as in the previous step. The reaction could also be monitored by TLC with a 100% EtOAc as the solvent. (Rf=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything; went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area by HPLC, R-isomer below level of detection) of 4 as a slightly tan powder. $[\alpha]D^{25}=22.0°$ (c=0.20, MeOH), m.p 107 ° C.; $^{13}C$ NMR (75 MHz, $CDCl_3$, ppm) 170.1,154.5, 79.8, 58.7, 50.6, 46.6, 43.6, 43.4, 28.6, 28.3.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A regioselective process for synthesizing any enantiomer of cis-1-amino-2-indanol or mixture of said enantiomers, said process substantially retaining the stereochemical integrity of the carbon-oxygen bond at C-2 in the indene oxide starting material, wherein the process comprises the steps of
   (a) providing one equivalent of indene oxide dissolved in a solvent and, optionally, a co-solvent, said solvent selected from an alkyl nitrile or aryl nitrile;
   (b) mixing thereto about two equivalents of an acid, said acid selected from a strong protic acid or a Lewis acid or an organic acid, and maintaining thereafter the temperature of the resulting mixture between about −70° C. and about +30° C. for a time period of between about 0.25 hour and about 6.0 hours;
   (c) adding excess water to effect hydrolysis, and stirring for a time period of between about 0.5 hour and about 8.0 hours, at a temperature of between about 25° C. and about 100° C., to give the, corresponding enantiomer of cis-1-amino-2-indanol, or mixture of said enantiomers.

2. A regioselective process, wherein (1S,2R)-indene oxide is substantially converted to 1S-amino-2R-indanol, comprising the steps of:
   (a) providing one equivalent of (1S,2R)-indene oxide dissolved in a solvent and, optionally, a co-solvent, said solvent selected from an alkyl nitrile or aryl nitrile;
   (b) mixing thereto about two equivalents of an acid, said acid selected from a strong protic acid or a Lewis acid or an organic acid, and maintaining thereafter the temperature of the resulting mixture between about −70° C. and about +30° C. for a time period of between about 0.25 hour and about 6.0 hours;
   (c) adding excess water to effect hydrolysis, and stirring for a time period of between about 0.5 hour and about 8.0 hours, at a temperature of between about 25° C. and about 100° C., to give 1S-amino-2R-indanol substantially free of any other enantiomer.

3. A regioselective process, wherein (1R,2S)-indene oxide is substantially converted to 1R-amino-2S-indanol, comprising the steps of:
   (a) providing one equivalent of (1R,2S)-indene oxide dissolved in a solvent and, optionally, a co-solvent, said solvent selected from an alkyl nitrile or aryl nitrile;
   (b) mixing thereto about two equivalents of an acid, said acid selected from a strong protic acid or a Lewis acid or an organic acid, and maintaining thereafter the temperature of the resulting mixture between about −70° C. and about +30° C. for a time period of between about 0.25 hour and about 6.0 hours;
   (c) adding excess water to effect hydrolysis, and stirring for a time period of between about 0.5 hour and about 8.0 hours, at a temperature of between about 25° C. and about 100° C., to give 1R-amino-2S-indanol substantially free of any other enantiomer.

4. A regioselective process of synthesizing 1S-amino-2R-indanol, comprising the steps of
   (a) providing ,one equivalent of (1S,2R)-indene oxide dissolved in acetonitrile and, optionally, a co-solvent;
   (b) mixing thereto about two equivalents of an acid selected from methanesulfonic acid or $H_2SO_4$-$SO_3$, and maintaining thereafter the temperature at about −10-25° C. for a time period of between about 30 minutes and about 2.5 hours;
   (c) adding excess water to effect hydrolysis, and stirring for time period between about 2 and about 5 hours, at a temperature range between about 45° C. and about 100° C., to give 1S-amino-2R-indanol substantially free of any other enantiomer.

5. A regioselective process of synthesizing 1R-amino-2S-indanol, comprising the steps of
   (a) providing one equivalent of (1R,2S)-indene oxide dissolved in acetonitrile and, optionally, a co-solvent;
   (b) mixing thereto about two equivalents of an acid selected from methanesulfonic acid or $H_2SO_4$-$SO_3$, and maintaining thereafter the temperature at about −10°-25° C. for a time period of between about 30 minutes and about 2.5 hours;
   (c) adding excess water to effect hydrolysis, and stirring for time period between about 2 and about 5 hours, at a temperature range between about 45° C. and about 100° C., to give 1R-amino-2S-indanol substantially free of any other enantiomer.

* * * * *